US00PP30350P2

(12) United States Plant Patent
Olesen

(10) Patent No.: US PP30,350 P2
(45) Date of Patent: Apr. 9, 2019

(54) MINIATURE ROSE PLANT NAMED 'POULPAH091'

(50) Latin Name: *Rosa hybrida*
Varietal Denomination: Poulpah091

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/731,979

(22) Filed: Sep. 5, 2017

(51) Int. Cl.
*A01H 5/02* (2018.01)

(52) U.S. Cl.
USPC ..... Plt./120

(58) Field of Classification Search
USPC ..... Plt./116, 119, 120, 121, 123, 126, 127, Plt./128, 141, 146, 147, 148
CPC ..... A01H 5/02; A01H 5/0222; A01H 6/749
See application file for complete search history.

(56) References Cited

U.S. PATENT DOCUMENTS

PP29,261 P3 * 5/2018 Olesen ..... Plt./120

OTHER PUBLICATIONS

Poulsen Roser A/S Fergie Hit retrieved on Jul. 31, 2018, retrieved from the Internet at http://de.poulsenroses.eu/sortiment/rosen-collectionen/patiohit/fergie-hit.aspx, one page. (Year: 2018).*

* cited by examiner

*Primary Examiner* — June Hwu

(57) ABSTRACT

A new garden rose plant of the Miniature class which has abundant, peach blend flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah091'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpah091', originated as a single seedling from the stated cross.

The new variety may be distinguished from its male pollen parent and female seed parent primarily by the following characteristics. The male pollen parent plant grows to a height of 65 cm while the new variety grows to a height of 40 cm. The female seed parent has near white flowers, while the new variety has peach blend flowers.

The objective of the hybridization of this rose variety was to create a new and distinct variety with unique qualities, such as:

1. Uniform and abundant peach blend flowers;
2. Vigorous, but compact growth when propagated on its own roots;
3. Exceptional disease resistance.

This combination of qualities is not present in previously available commercial cultivars of this type, known to the inventor, and distinguish 'Poulpah091' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpah091' was selected in the spring of 2012 by the inventor as a single plant from the progeny of the aforementioned hybridization.

Asexual reproduction of 'Poulpah091' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpah091' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah091'.

Specifically illustrated in FIG. 1 of the drawings are open flowers at various stages of development, petals detached, sepals detached, showing receptacle and pedicel.

DETAILED DESCRIPTION OF THE VARIETY

Figure 1:
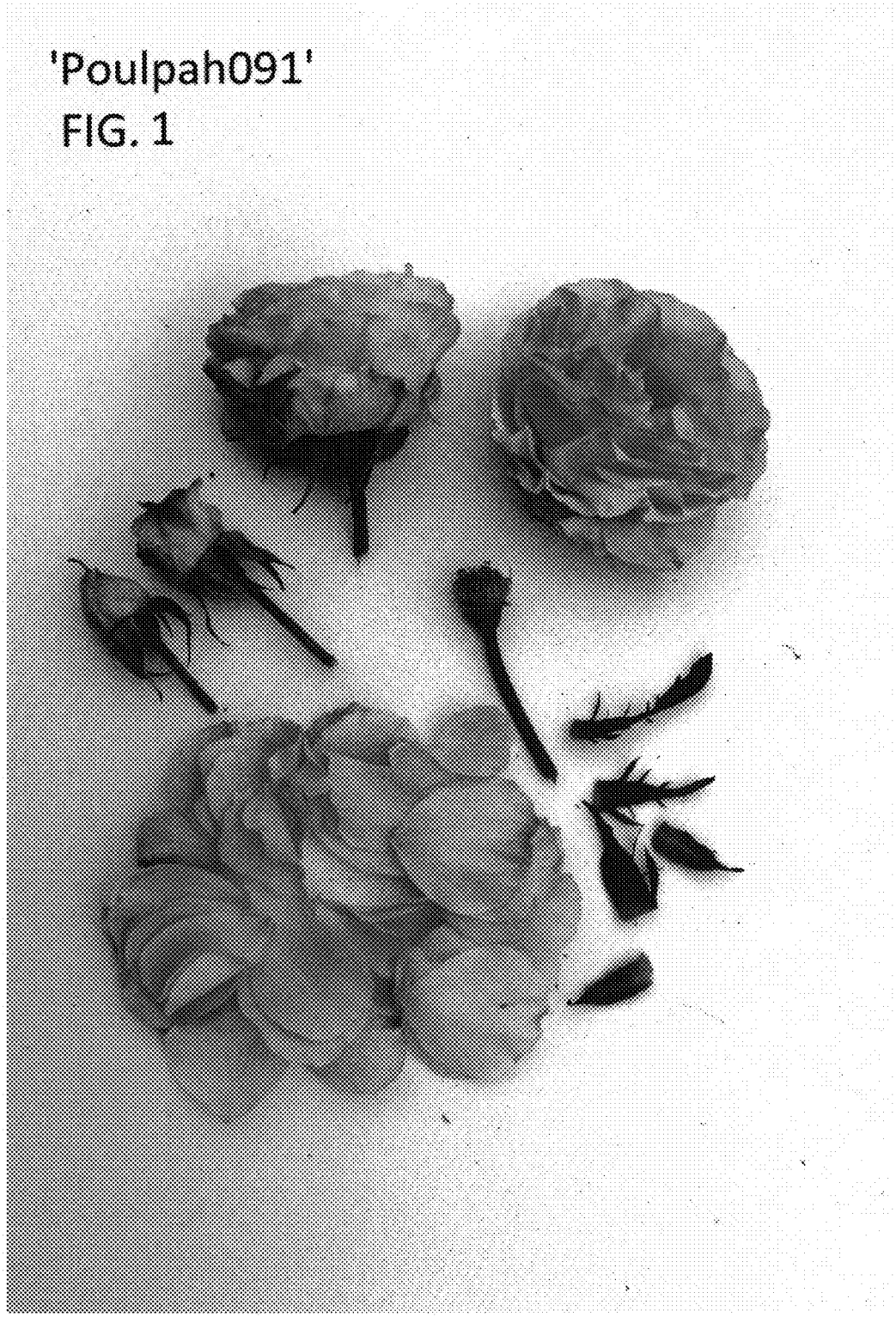
Figure 2:
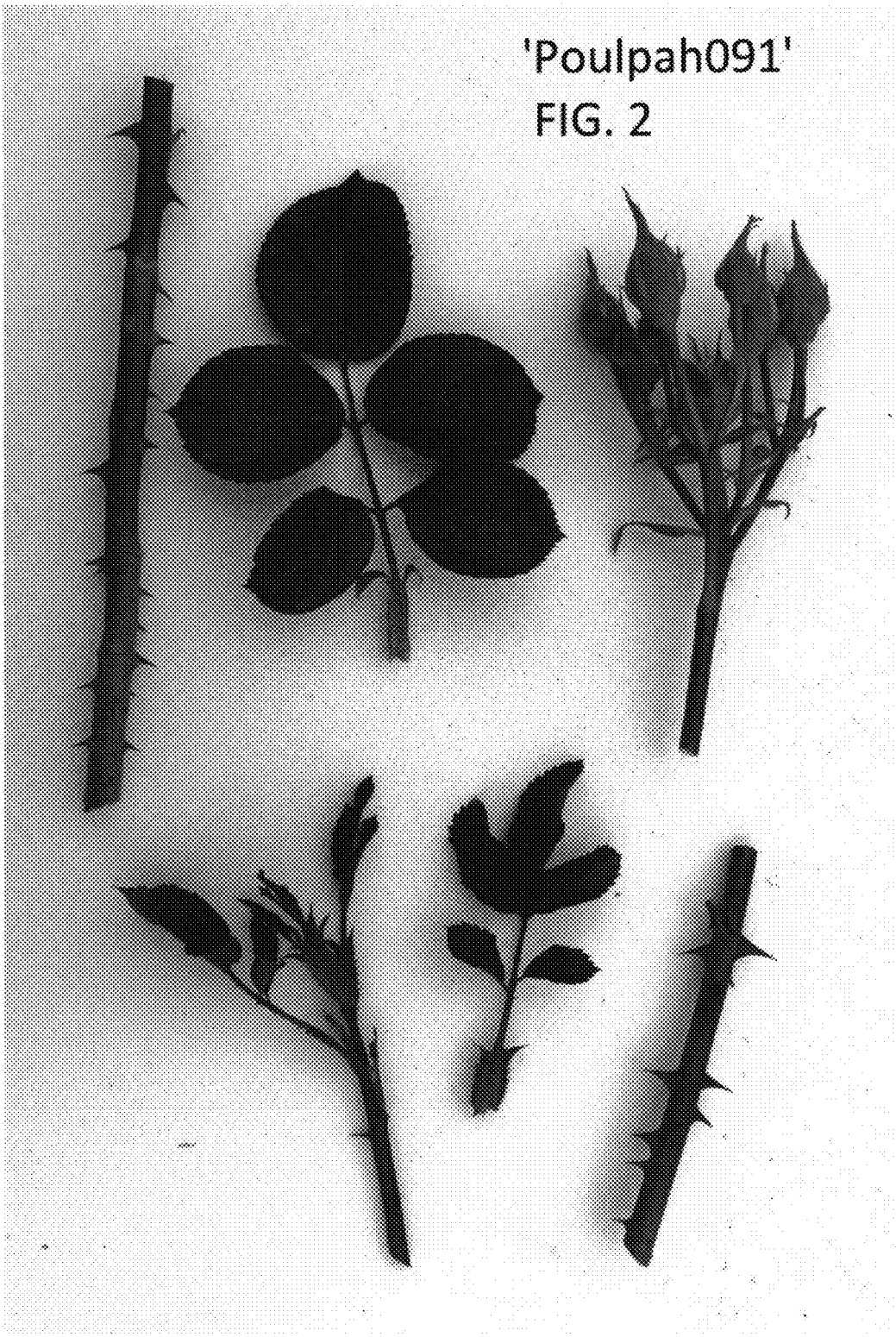
FIG. 2 shows a cluster of flower buds on a branch, juvenile and mature leaves and stems. Plants shown are 2 years of age.

The following is a description of 'Poulpah091', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpah081', U.S. Plant Pat. No. 29,261, are compared to 'Poulpah091' in Chart 1.

CHART 1

| | 'Poulpah091' | 'Poulpah081' |
|---|---|---|
| Petal Count | 55 | 60 |
| Flower Diameter | 80 mm | 60 to 70 mm |
| General Tonality of Flower Color | Yellow-Orange Group 19B with intonations of Orange Group 24C | Yellow-Orange Group 20C |

FLOWER AND FLOWER BUD

Blooming habit: Continuous.

Flower bud:

*Size.*—Upon opening, 23 mm in length from base of receptacle to end of bud. Bud diameter is 14 mm.

*Bud form.*—Ovoid.

*Bud color.*—As sepals divide petals are Orange-White Group 159B and Green-White Group 157A

*Sepal inner surface.*—Color: Yellow-Green Group 146D. Surface: Lightly pubescent.

*Sepal outer surface.*—Color: Yellow-Green Group 146A with intonations of Greyed-Red Group 180A. Texture: Smooth.

*Sepal shape.*—Apex: Cirrhose. Base: Flat at union with receptacle.

*Sepal margin.*—Margins have strong foliaceous appendages on three of the five sepals.

*Sepal size.*—50 mm long, 17 mm wide.

*Receptacle.*—Texture: Smooth. Size: 7 mm in height, 11 mm wide. Color: Yellow-Green Group 144A with intonations of Greyed-Red Group 180A. Shape: Campanulate.

*Pedicel.*—Surface: Smooth. Length: 45 mm. Diameter: 3 mm on average. Color: Yellow-Green Group 144A with intonations of Greyed-Red Group 179A. Strength: Strong.

*Peduncle.*—Length: 2 to 3 cm. Diameter: About 3 mm. Color: Yellow-Green Group 144A with intonations of Greyed-Red Group 179A. Texture: Smooth.

Flower bud development: Flower buds are borne in clusters of 5 to 9 flower buds per stem.

Flower bloom:

*Fragrance.*—Moderate.

*Duration.*—The blooms have a duration on the plant of approximately 20 days. Petals cling after flowers have fully matured.

*Size.*—Flower diameter is 80 mm when open. Flower depth is 45 mm.

*Flower shape.*—Rosette, very double flower with many slightly overlapping petals of different sizes.

*Shape of flower, side view.*—The upper portion is concave. Flattened convex.

Petalage: Under normal conditions, flowers have about 55 petals.

General tonality of flower: Open flowers are Yellow-Orange Group 19B with intonations of Orange Group 24C.

Petal color:

*Upon opening, outer petals.*—Upper surface: Red Group 36C blended with Red Group 37D at marginal and middle zone. A large basal petal spot of Yellow Group 4C. Lower surface: A large basal petal spot of Yellow Group 3C. Middle zone Yellow-White Group 158A. Middle to outer zone has intonations of Red Group 38D. Guard petals show Green-White Group 157A and Greyed-Red Group 179A.

*After opening, inner petals.*—Upper surface: Marginal zone is Orange Group 27A, Yellow-Green Group 4C towards basal zone. Lower surface: Marginal zone is Orange Group 27A, Yellow-Green Group 4C towards basal zone.

Petals:

*Petal reflex.*—None.

*Margin.*—Entire and uniform. Strong to moderate undulations.

*Shape.*—Broad and elliptic. Apex shape: Rounded. Base shape: Acute.

*Size.*—40 mm (l)×40 mm (w).

*Texture.*—Smooth.

*Thickness.*—Average.

Petaloids: None observed.

Reproductive flower parts:

*Pollen.*—None observed.

*Anthers.*—Size: 2 mm in length. Color: Yellow-Orange Group 16B. Quantity: 60 on average.

*Filaments.*—Color: Yellow-Orange Group 17A. Length: 6 mm.

*Pistils.*—Length: 7 mm. Quantity: 40 on average.

*Stigmas.*—Color: Greyed-Yellow Group 161D.

*Styles.*—Color: Red Group 51B.

*Location of stigmas.*—Superior in location relative to the length of the filaments and the height of the anthers.

*Hips.*—None Observed.

PLANT

Plant growth: Upright. Plants are 40 cm in height, and 35 cm wide.

Stems:

*Color of juvenile growth.*—Yellow-Green Group 144A with intonations of Greyed-Purple Group 183D.

*Color of mature growth.*—Yellow-Green Group 144A.

*Length.*—Canes are about 30 cm from the base of the plant to the flowering portion.

*Diameter.*—About 9 mm.

*Internodes.*—On mature canes about 35 mm between nodes.

*Surface texture.*—Young wood: Smooth. Older wood: Somewhat rough with small prickles.

Long prickles:

*Incidence.*—9 prickles per 10 cm of stem.

*Size.*—Average length of prickles on mature stems is 10 mm.

*Shape.*—Upper portion is linear. Lower portion is concave.

*Color.*—Juvenile prickles: Greyed-Red Group 180A. Mature prickles: Greyed-Red Group 179B.

Plant foliage:

*Compound leaf.*—145 mm (l)×110 (w).

*Quantity.*—3 leaves per 10 cm of stem on average.

*Leaf bearing angle to the stem.*—45 degrees.

*Color of juvenile foliage*.—Upper side: Greyed-Red Group 178A. Lower side: Greyed-Red Group 178A.

*Color of mature foliage*.—Upper side: Yellow-Green Group 147A. Lower side: Yellow-Green Group 146B.

Plant leaves and leaflets:

*Stipules*.—Size: 25 mm long, 5 mm wide. Quantity: 2 per compound leaf. Shape: Linear, slightly broad based with outward extending apices. Margins: Finely serrated. Color: Yellow-Green Group 144A.

*Petiole*.—Length: 35 mm. Diameter: 2 mm. Upper surface color: Greyed-Red Group 178B. Lower surface color: Yellow-Green Group 144A. Surface texture: Smooth, with occasional stipitate glands.

*Rachis*.—Length: 60 mm. Upper surface color: Greyed-Red Group 178B. Lower surface color: Yellow-Green Group 144A. Surface texture: Smooth, with occasional stipitate glands.

*Leaflet*.—Quantity: Normally 5 leaflets. Margins: Serrated. Undulations absent. Size: Terminal leaflets are about 55 mm long, 45 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var rosae, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Miniature rose class named 'Poulpah091', substantially as illustrated and described herein, due to its abundant peach blend flowers, disease resistance, and extended period of bloom.

* * * * *

'Poulpah091'

'Poulpah091'